US005885827A

United States Patent [19]
Wabl et al.

[11] Patent Number: 5,885,827
[45] Date of Patent: Mar. 23, 1999

[54] EUKARYOTIC HIGH RATE MUTAGENESIS SYSTEM

[75] Inventors: Matthias Wabl; Jürgen Bachl, both of San Francisco, Calif.

[73] Assignee: The Regents of the Universtiy of California, Oakland, Calif.

[21] Appl. No.: 589,112

[22] Filed: Jan. 23, 1996

[51] Int. Cl.$^6$ .................................................. C12N 15/00
[52] U.S. Cl. .................................... 435/320.1; 435/372.2
[58] Field of Search ............................ 435/320.1, 240.2, 435/172.1, 372.2; 530/412, 300–350; 424/130.1

[56] References Cited

U.S. PATENT DOCUMENTS 5,371,009  12/1994  Neuberger et al. ..................... 435/355

OTHER PUBLICATIONS

Adetugbo, et al.; "Review Article—Molecular analysis of spontaneous somatic mutants"(1977) Nature 265, 299–304.
Azuma, et al.; "Mutations of the chloramphenicol acetyl transferase transgene driven by the immunoglobulin promoter and intron enhancer" International Immunology 5, No. 2, 121–130.
Berek, et al.; "Molecular events during maturation of the immune response to oxazolone" (1985) Nature 316, 412–418.
Betz, et al.; "Elements Regulating Somatic Hypermutation of an Immunoglobulin κ Gene: Critital Role for the Intron Enhancer/Matrix Attachment Region" (1994) Cell 77, 239–248.
Betz., et al.; Passenger transgenes reveal intrinsic specificity of the antibody hypermutation mechanism: Clustering, polarity, and specific hot spots (1993) Proc. Natl. Acad. Sci. USA 90, 2385–2388.
Bothwell et al.; "Heavy Chain Variable Region Contribution to the NP $^b$ Family of Antibodies: Somatic Mutation Evident in a γ2a Variable Region" (1981) Cell 24, 625–637.
Brenner, et al.; "Origin of Antibody Variation"(1966) Nautre 211, 242–243.
Clarke, et al.; "Inter–And Intraclonal Diversity In The Antibody Response To Influenza Hemagglutinin" (1985) J. Exp. Med. 161, 687–704.
Crews, et al.; "A Single $V_H$ Gene Segment Encodes the Immune Response to Phosphorylcholine: Somatic Mutation is Correlated with the Class of the Antibody" (1981) Cell 25, 59–70.
Desiderio, et al.; "Insertion of N regions into heavy–chain genes is correlated with expression of terminal deoxytransferase in B cells" (1984) Nature 311, 752–755.
Gearhart, et al.; "Clusters of point mutations are found exclusively around rearranged antibody variable genes" (1983) Proc. Natl. Acad. Sci. USA 80, 3439–3443.
Gearhart, et al.; "IgG antibodies to phosphorylcholine exhibit more diversity than their IgM counterparts" (1981) Nature 291, 29–34.
Green, et al.; "Immunoglobulin variable region hypermutation in hybrids derived from a pre–B–and a myeloma cell line" (1995) Proc. Natl. Acad. Sci. USA 92:6304–6308.

Griffiths, et al.; "Somatic mutation and the maturation of immune response to 2–phenyl oxazolone" (1984) Nature 312, 271–275.
Grosschedl, et al.; "Introduction of a μ Immunoglobulin Gene into the Mouse Germ Line: Specific Expression in Lymphoid Cells and Synthesis of Functional Antibody" (1984) Cell 38, 647–658.
Grosschedl, et al.; "Cell–Type Specificity of Immunoglobulin Gene Expression is Regulated By at Least Three DNA Sequence Elements" (1985) Cell Vol. 41, 885–897.
Jack, et al.; "High rates of deletions in the constant region segment of the immunoglobin μ gene" (1987) Proc. Natl. Acad. Sci. USA 84, 4934–4938.
Jack, et al.; "Looping out and deletion mechanism for the immunoglobulin heavy–chain class switch" (1988) Proc. Natl. Acad. Sci. USA 85, 1581–1585.
Jacob, et al.; "Intraclonal generation of antibody mutants in germinal centres" (1991) Nature 354, 389–3892.
Johnston, et al.; "A Shuttle Vector System for the Investigation of Immunoglobulin Gene Hypermutation: Absence of Enchanced Mutability in Intermediate B Cell Lines" (1992) Molecular Immunology 29:1005–1011.
Kim, et al.; "Antibody Diversity: Somatic Hypermutation of Rearranged $V_H$ Genes"(1981) Cell 27, 573–581.
Lebeque, et al.; "Boundaries of Somatic Mutation in Rearranged Immunoglobulin Genes: 5' Boundary Is Near the Promoter, and 3' Boundary Is ~1 kb From V(D)J Gene" (1990) J. Exp. Med. 172, 1717–1727.
Lederberg, J.; "Genes and Antibodies—Do antigens bear instructions for antibody specificity or do they select cell lines that arise by mutation" (1959) Science 129, 1649–1653.
Manser, et al.; "Influence of Clonal Selection of the Expression of Immunoglublin Variable Region Genes" (1984) Science 226, 1283–1288.
Max, Edward E.; Funamental Immunology, Chapter 10, Immuglobulins –Molecular Genetics, Third Edition, Ed. William Paul, 1993, pp. 315–382.
McKean, et al.; "Generation of antibody diversity in the immune response of BALB/C mice to influenza virus hemagglutinin" (1984) Proc. Natl. Acad. Sci USA 81, 3180–3184.

(List continued on next page.)

Primary Examiner—James Ketter
Assistant Examiner—Irem Yucel
Attorney, Agent, or Firm—Cooley Godward LLP

[57] ABSTRACT

A method is provided for performing saturation mutagenesis on a target gene by exploiting the immunoglobulin hypermutation system. A target gene is cloned into an expression vector containing immunoglobulin enhancer fragments that effect hypermutation, and this construct is then transfected into an immunoglobulin mutator cell, typically of pre-B lymphocyte lineage. The target gene is permitted to hypermutate at a rate approaching that of $10^{-4}$/bp/generation as the cells are cultured to a desired density. The variant polypeptides encoded by the hypermutated target gene can then be selected.

33 Claims, 3 Drawing Sheets

OTHER PUBLICATIONS

Meyer, et al.; "High rate of somatic point mutation in vitro in and near the variable–region segment of an immunoglobulin heavy chain gene" (1986) Proc. Natl. Acad. Sci. USA 83, 6950–6953.

Meyer, et al.; "The immunoglobulin κ locus contains a second, stronger B–cell–specific enhancer which is located downstream of the constant region" (1989) EMBO J. 8, 1959–1964.

Meyer, et al.; "The importance of the 3'–enhancer region in immunoglobulin κ gene expression" (1990) Nucleic Acid Res. 18, 5609–5615.

Milstein, et al.; "Expression of Antibody Genes in Tissue Culture: Structural Mutants and Hybrid Cells" (1978) Third Decennial Review Conference, National Cancer Institute Monographs 48, 321–330.

Myers, et al.; "Fine Structure Genetic Analysis of a β–Globin Promoter" (1986) Science 232 (4750) pp. 613–618.

Nolan, et al.; "Fluorescence–activated cell analysis fo viable mammalian cells based on β–D–galactosidase activity after transduction of Escherichia coli lacZ" (1988) Proc. Natl. Acad. Sci. USA 85, 2603–2607.

Oancea, et al.; "An improved system of somatic cell molecular genetics for analyzing the requirements of Ig synthesis and function" (1994) Int. Immunol. 6(8) :1161–1168.

Rogerson, et al.; "Mapping the Upstream Boundary of Somatic Mutations In Rearranged Immunoglobulin Transgenes and Endogenous Genes" (1994) Mol. Immunol. 31, 83–98.

Rudikoff, et al.; "Somatic diversification of immunoglobulins" (1984) Proc. Natl. Acad. Sci USA 81, 2162–2165.

Sablitzky, et al.; "Somatic mutation and clonal expansion of B cells in an antigen–drives immune response" (1985) EMBO J. 4, 345–350.

Selsing, et al.; "Somatic Mutation of Immunoglobulin Light–Chain Variable–Region Genes" (1981) Cell 25, 47–58.

Sharpe, et al.; "Somatic hypermutation of immunogloublin κ may depend on sequences 3' of Cκ and occurs on passenger transgenes" (1991) EMBO vol. 10 No. 8 pp. 2139–2145.

Shulman, et al.; "Mutations Affecting the Structure and Function of Immunoglobulin M" (1982) Molec. Cell Biol. 2, 1033–1043.

Thomas, et al.; "Site–Directed Mutagenesis by Gene Targeting in Mouse Embryo–Derived Stem Cells" (1987) Cell 51, 503–512.

Umar, et al.; "Mutation in a reporter gene depends on proximity to and transcription of immunoglobulin variable transgenes" (1991) Proc. Natl. Acad. Sci. USA 88:4902–4906.

Wabl, et al.; "Hypermutation at the immunoglobulin heavy chain locus in a pre–B–cell line" (1985) Proc. Natl. Acad. Sci. USA 82, 479–482.

Weber, et al., "Position of the Rearranged Vκ and Its 5' Flanking Sequences Determines the Location of Somatic Mutations in the Jκ Locus"(1991) J. Immunol. 146, 3652–3655.

Weigert, et al.; "Variability in the Lambda Light Chain Sequences of Mouse Antibody" (1970) Nature 228, 1045–1047.

Yelamos, et al.; "Targeting of non–Ig sequences in place of the V segment by somatic hypermutation" (1995) Nature 376, 376:225–229.

Zhu, et al.; "A well–differentiated B–cell line is permissive for somatic mutation of a transfected immunoglobulin heavy–chain gene"(1995) Proc. Natl. Acad. Sci. USA 92, 2810–2814.

Ziegner, et al.; "Development of antibody diversity in single germinal centers: selective expansion of high–affinity variants" (1994) Eur. J. Immunol. 24, 2393–2400.

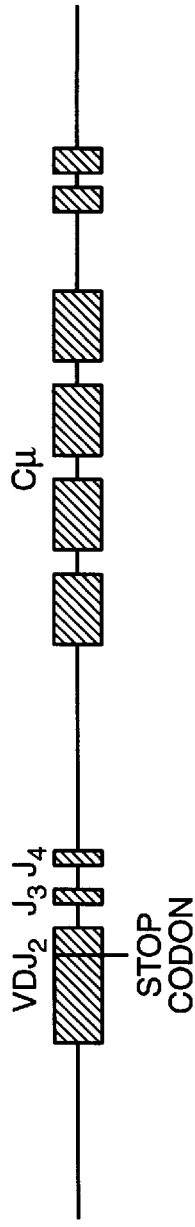
FIG._2A
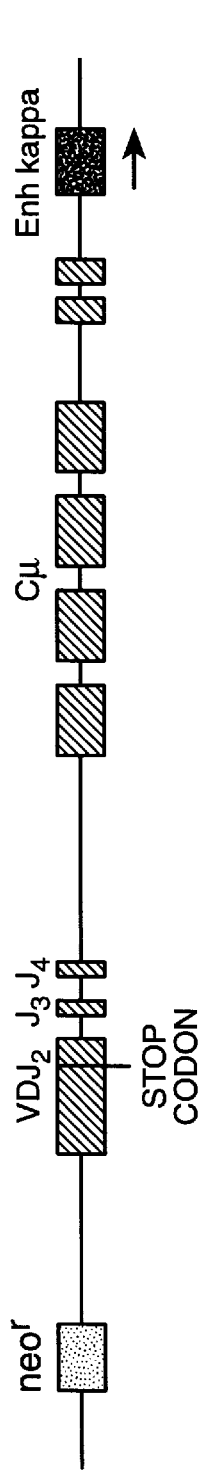
FIG._2B
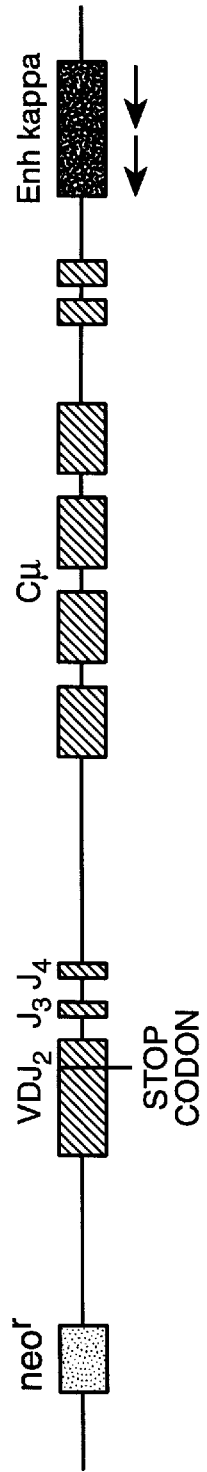
FIG._2C
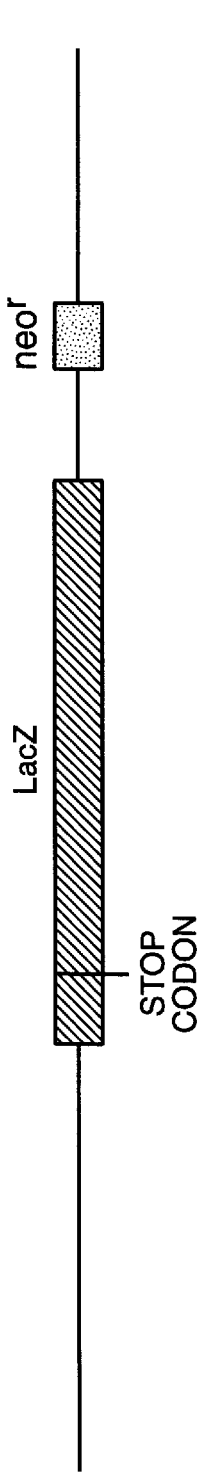
FIG._2D

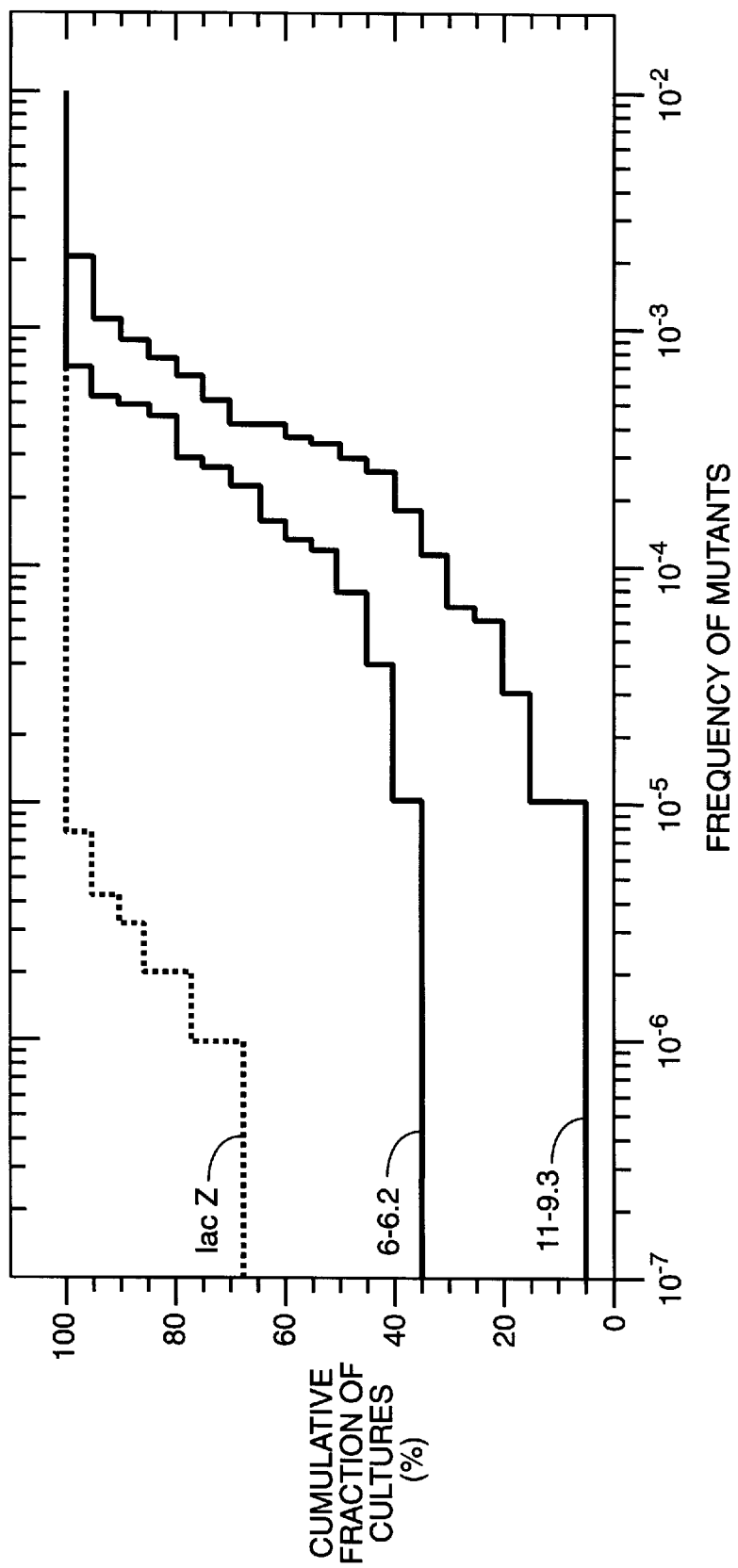

EUKARYOTIC HIGH RATE MUTAGENESIS SYSTEM

ACKNOWLEDGEMENTS

This invention was supported in part by Grant No. GM37599 from the National Institutes of Health. The U.S. Government may have rights in this invention.

INTRODUCTION

1. Technical Field

This application relates to a eukaryotic high rate mutagenesis system useful for performing saturation mutagenesis over the length of a target gene with a minimum of manipulation, yielding mutant proteins capable of undergoing any post-translational modifications that may be required for biological activity.

2. Background

To date, there are several ways to modify a given protein by mutagenesis. In site-directed mutagenesis, the gene encoding the protein of interest is cloned into a prokaryotic vector, and mutations are introduced by hybridizing the gene with an oligonucleotide that contains the desired mutation, followed by a replication event that completes the synthesis of the new, mutated gene. In saturation mutagenesis the gene is altered randomly. In so-called scanner mutagenesis, a subfraction of codons encoding a particular amino acid residue is replaced, e.g., by alanine. In another approach the error rate of polymerase chain reaction is used to introduce mutations; the error rate is due to the intrinsic infidelity of the polymerase used in PCR and can be increased by altering the nucleotide ratio. Mutagenesis in *Escherichia coli* can be carried out using mutator strains defective in DNA repair. And, finally, mutations in endogenous genes in cell lines are introduced by chemicals or by radiation. For example, Myers et al., Science May 2 1986, 232 (4750) p613-8, describe a procedure for saturation mutagenesis by chemical treatment of single-stranded cloned DNA which obtained more than 100 single base substitutions within a promoter.

Whatever the method of generating the mutants, the function of the individual mutants is subsequently assessed by transfecting individual mutant genes into the cells that are used for the biological read out. In order to find an interesting mutant, one has to make an educated guess of where to modify the protein or investigate the properties of a large library of mutants.

The present invention allows for random mutagenesis of an entire gene in one step without having to incrementally randomize particular domains and thus has a number of advantages over other random mutagenesis methods. One advantage is one-step cloning. Unlike other systems where, e.g., degenerate oligos are used to randomize a particular region of a gene and thus require a heterogeneous cloning step, this invention involves the cloning of a homogeneous population, thereby removing any doubt as to lost representation due to inefficient ligation or transformation. Another advantage is speed. Other systems require stepwise mutagenesis of particular codons or regions of the genes, each set requiring a round of vector construction, transformation, and expression. Examples are ala-scanning and phage display. This invention is particularly useful for those polypeptides for which glycosylation is required for activity. Bacterial systems cannot provide glycosylated peptides, while yeast and baculovirus systems that can have other disadvantages, including (1) glycosylation that is different than that occurring in mammalian cells; (2) that baculovirus systems are slow and are lytic systems, which can complicate the process; and (3) that yeast expression systems can sometimes be limited by the primary amino acid structure of the polypeptide (e.g., some are sensitive to cleavage). Unlike combinatorial peptide chemistry, the system of the present invention utilizes basic molecular biology techniques and requires minimal equipment, so that a laboratory can practice the invention with little prior expertise or expense by following the description and examples set out in this specification.

This invention exploits an immunoglobulin hypermutation system to perform random mutagenesis on heterologous target genes. Although mutations are, in general, detrimental to the individual, they are the substrate upon which evolution works. The intrinsic fidelity of the enzymes involved in DNA replication is not very high, and, to reduce the number of mutations, elaborate error-checking and repair systems have evolved in mammals. But mutations in immunoglobulin genes add to antibody diversity and help the immune system to cope with the large diversity of threatening microorganisms, which is itself mutational in origin.

The mechanism for hypermutation is unknown, but it is known that regions of DNA known as enhancers are somehow involved in hypermutation. Over thirty five years ago, it was suggested that somatic mutations were the major source of antibody diversity (Lederberg, J. et al. (1959) Science 129, 1649). Later, Brenner and Milstein (1966) Nature 211, 242–243, proposed that an enzyme complex would actively place mutations, and thus cause hypermutation, at the immunoglobulin locus. The Brenner-Milstein model bears an uncanny resemblance to the way in which untemplated nucleotides, so-called N regions, are added at the DJ and VD junctions during immunoglobulin heavy chain gene rearrangement (Desiderio et al. (1984) Nature 311, 752–755), a process that was discovered almost 20 years after the model was proposed. The early work of Weigert et al. (1970) Nature 228, 1045–1047, showed that somatic point mutations indeed make a major contribution to the diversity of the λ light chain in the mouse. Although the tone had already been set by those studies on myelomas, it came as somewhat of a surprise that the genes encoding the immunoglobulin chains expressed in the secondary immune response carried so many mutations of somatic origin (Gearhart et al., (1981) Nature 291, 29–34; Bothwell et al., (1981) Cell 24, 625–637; Crews et al., (1981) Cell 25, 59–70; Kim et al., (1981) Cell 27, 573–581; Selsing et al., (1981) Cell 25, 47–58; Gearhart et al., (1983) Proc. Natl. Acad. Sci. USA 80, 3439–3443; McKean et al., (1984) Proc. Natl. Acad. Sci. USA 81, 3180–3184; Manset et al., (1984) Science 226, 1283–1288; Rudikoff et aL, (1984) Proc. Natl. Acad. Sci. USA 81, 2162–2165; Berek et al., (1985) Nature 316, 412–418; Clarke et al., (1985) J. Exp. Med. 161, 687–704; Sablitzky et al., (1985) EMBO J. 4, 345–350; Griffiths et al., (1984) Nature 312, 271–275). Because of the high frequency of mutations, the process that produced these somatic point mutations earned the epithet "hypermutation." If hypermutation is to contribute to affinity maturation, it must be active during B-cell proliferation after antigenic stimulation. Indeed, cells undergoing hypermutation are found in the germinal centers, where the B-cell response in large part takes place (Jacob et al., (1991) Nature 354, 389–3892; Ziegner et al., (1994) Eur. J. Immunol. 24, 2393–2400).

In the heavy chain genes, the segments encoding the immunoglobulin variable (V) region is the 'epicenter' of mutation, with the frequency of mutation decreasing progressively in both 5' and 3' directions. The area of hypermutation of about 2 kb includes the flanking regions. The 5' boundary near the promoter region is distinct; the 3' boundary near the enhancer region is more loosely defined. The actual V gene segment is not needed to trigger the process. Mutator action is restricted to a region flanked by the V gene leader intron and intron enhancer (Lebecque et al., (1990) J. Exp. Med. 172, 1717–1727; Weber et al., (1991) J. Immunol. 146, 3652–3655; Rogerson et al., (1994) Mol. Immunol. 31, 83–98; Rada et al., (1994) Eur. J. Immunol. 24, 1453–1457; Gonzalez-Femandez et al., (1994) Proc. Natl. Acad. Sci. 91, 12614–12618). However, the recognition sequence does not seem to be contained in the 5' portion containing the promoter, and both the kappa intron and kappa 3' enhancer regions were found to be essential for full hypermutation at the K locus (Betz et al., (1994) Cell 77, 239–248; Sharpe et al., (1991) EMBO J. 10, 2139–2145). Thus, there may well be more than one recognition sequence. Somatic mutation has also been linked to the direction of DNA replication (Rogerson et al., (1991) EMBO J. 10, 4331–4341).

Other groups have observed a lack of hypermutation when the kappa enhancer is omitted (Sharpe et al., *Fundamental Immunology*, Chapter 10, Third Edition, William Paul, 1993). Higher transcription is associated with a better somatic mutation rate as compared to a transgene construct lacking kappa enhancer. The kappa enhancer/matrix attachment region is essential for hypermutation in the immunoglobulin light chain (Betz et al., *Proc. Natl. Acad. Sci. USA* 90:2385–2388 [1993]; Yelamos et al, Nature 376:225–229 [1195]). Neuberger et al., U.S. Pat. No. 5,371,009, performed a functional dissection of the κ3' enhancer and identified a 53 bp region responsible for enhanced transcription. However, they do not disclose that the truncated κ enhancer element is functional for hypermutation. It may be that transcription and hypermutation are controlled by different regions or elements within the κ enhancer. The only hypermutation experiments conducted were done in a transgenic mouse comparing only constructs that did or did not include the 8 kb region 3' of $C_k$, which contains the entire 3' κ enhancer. There was no disclosure of hypermutation experiments performed using solely the 53 bp fragment. In addition, the transgene used in U.S. Pat. No. 5,371,009 was an antibody directed against phOX. The antibody was a chimeric gene fusing the V region from the mouse antibody to the corresponding C region from the rat antibody for detection purposes. There was no disclosure of hypermutation of a non-immunoglobulin. Although they suggest making a transgenic with a repertoire of high affinity human antibodies, Neuberger et al. do not consider hypermutation of heterologous genes. They suggest transforming a B-cell derived cell line with a vector containing heterologous genes only for the purpose of increasing expression levels by enhancing transcription.

Other groups have replaced the V gene segment in a light chain transgene by the bacterial sequences gpt and $neo^r$ in a construct that contained other elements needed for hypermutation (a promoter, the light chain major intron enhancer and 3' enhancer), and the bacterial sequences underwent hypermutation during an immune response (Yelamos et al., Nature 1995, 376:225–229). Azuma et al., International Immunology Vol. 5 No. 2 pp. 121–130, inserted the heterologous CAT reporter gene into a heavy chain gene, and the resulting construct was used to create a transgenic mouse for subsequent evaluation of hypermutation in vivo. Likewise, Umar et al., Proc. Natl. Acad. Sci. USA 88:4902–4906 [1991], inserted a heterologous reporter gene into a rearranged κ gene and used the product to create a transgenic mouse for subsequent evaluation of hypermutation in vivo. However, hypermutation in vivo does not provide a practical and efficient method of performing large scale saturation mutagenesis of a target gene.

Johnston et al., Molecular Immunology 29(708): 1005–1011 [1992], developed a shuttle vector system for the investigation of immunoglobulin gene hypermutation and observed an absence of enhanced mutability in intermediate B cell lines transfected with a VD segment and a portion of the heavy chain intron.

The present invention accomplishes this objective by providing an in vitro system for saturation mutagenesis that uses a mutator-positive cell line and a vector containing elements required for hypermutation. Mutations at the immunoglobulin loci have been studied in a lymphocyte mutator line by the present inventors since 1985 (Wabl et al., Proc Natl Acad Sci USA 82:479–482 [1985]). We have established that hypermutation can occur in vitro in the murine pre-B cell line 18–81 (Wabl et al., (1985) Proc. Natl. Acad. Sci. USA 82, 479–482; Meyer et al., (1986) Proc. Natl. Acad. Sci. USA 813, 6950–6953). The proximate cause for hypermutation, the putative immunoglobulin mutator system (mutator), increases the mutation rate at the gene segments encoding the endogenous V region by a factor of at least $10^5$. The mutator does not work efficaciously at the $C\mu$ gene segment (Jack et aL, (1987) Proc. Natl. Acad. Sci. USA 84, 4934–4938), nor at the B2m locus (Wabl et aL, (1987) Immunol. Rev. 96, 91–107). It does not seem to be active at the plasma cell stage (Wabl et al., (1985) Proc. Natl. Acad. Sci. USA 82, 479–482), which represents the final stage in the differentiation of a B lymphocyte. We generated immunoglobulin heavy chain gene constructs with all the cis-acting elements necessary for hypermutation comparable to the rate of the endogenous gene segments encoding the V region. The laboratory of Matthew Scharff also described a mutator assay using the 18–81 cell line. However, in these publications the 3' κ enhancer is not included, and the mutation rates are orders of magnitude lower than what the present inventors have achieved using the high-rate mutagenesis system of the invention (Zhu et al., Proc Natl Acad Sci USA 92:2810–2814 [1995]; Green et al., Proc Natl Acad Sci USA 92:6304–6308 [1995]). Recently, we have shown that the region between a promoter and the heavy chain intron enhancer is hypermutated in a construct in which the kappa 3' enhancer is positioned 3' of the heavy chain enhancer. This construct, depicted in FIG. 2, contains the $C\mu$ gene inserted in this region between the promoter and the heavy chain enhancer. As mentioned above, the endogenous $C\mu$ gene is not hypermutated. However, when removed from its native configuration and cloned into a vector in proximity to the heavy chain intronic enhancer fragment and the 3' Kappa enhancer fragment, the $C\mu$ gene underwent hypermutation. These results validate the efficaciousness of the high-rate mutagenesis system of the present invention.

What has yet to be provided in the art is a system that can perform rapid mutagenesis over long pieces of DNA and maintain the structural and functional integrity of the protein product. The advantages of the present invention over current mutagenesis techniques are as follows: (1) it is fast—only a single cloning step is required for saturation mutagenesis; (2) it provides a high mutation rate approaching $10^{-4}$/base pair/cell/generation, thereby assuring full representation of all possible mutations; (3) it immediately delivers a "final" product as the protein variant is properly processed (e.g., glycosylated); and (4) it can be coupled with a selection system of choice.

OBJECTS OF THE INVENTION

It is an object of the invention to provide a eukaryotic mutagenesis system that can generate protein variants of biological and medical interest at a fast rate. It is a further object of the invention to provide a eukaryotic mutagenesis system requiring only a single cloning step for saturation mutagenesis that results in a protein variant that is properly processed (e.g., post-translationally modified) and that can be coupled with a selection system of choice that identifies potentially useful mutants.

SUMMARY OF THE INVENTION

The invention exploits the murine immunoglobulin hypermutation system to perform random mutagenesis on heterologous target genes. The invention, however, is not limited to the use of murine components. For example, human components can also be used. The invention employs an expression vector containing the heavy chain large intronic enhancer and the kappa light chain 3' enhancer. The gene encoding a protein of choice is cloned into a cassette so as to be under the control of a promotor and in proximity to immunoglobulin enhancers. The construct is then transfected into a mutator-positive cell line, where it is mutated at a rate approaching that seen for naturally occurring hypermutation of immunoglobulin genes, which is $10^{-4}$ per base pair per cell generation. A selection system particular to the properties of the target protein is utilized to identify and recover the favored mutations in some embodiments.

One aspect of the invention is a hypermutation-competent expression vector comprising a promoter positioned to drive a target gene and at least two immunoglobulin enhancers in close proximity to the target gene. Another aspect of the invention is a cell transfected with a hypermutation-competent expression vector. Another aspect of the invention is a method for performing saturation mutagenesis of a target gene by transfecting an immunoglobulin-mutator-positive cell with a hypermutation-competent expression vector into which has been cloned a target gene, permitting the target gene to hypermutate, and selecting a variant with desired characteristics. Another aspect of this invention is an antibody or polypeptide obtained by this method.

BRIEF DESCRIPTION OF THE DRAWINGS

FIGS. 2A–2D are schematic diagrams of plasmids used to monitor mutator activity. FIG. 2A, endogenous configuration of the silent V2 allele (45) in the cell line 18–81. The V2 allele is functionally rearranged but no $\mu$ chain is expressed because of a TAG termination codon within the D segment. FIG. 2B, plasmid phyp #1 containing the 3' κ enhancer in addition to the $\mu$ gene as in FIG. 2A. FIG. 2C, plasmid phyp #2, differing from phyp #1 by the two 3' κ enhancers in tandem, which are oriented in the opposite direction, indicated by arrows. FIG. 2D, plasmid ptk-LacZ-Stop containing a TGA termination codon, which prevents expression of β galactosidase activity.

FIG. 3 is a schematic diagram of the cumulative distribution of reversion frequencies in cultures of the two independent clones 6–6.2 (transfected with phyp#2) and 11–9.3 (phyp#1), and clone lacZ (transfected with ptk-LacZ-Stop). Y-axis: cumulative fraction of cultures, in percent on a linear scale. X-axis: frequency of mutants ($\mu$ producers and lacZ producers, respectively) in a given culture, on a logarithmic scale.

DESCRIPTION OF SPECIFIC EMBODIMENTS

Figure 1:
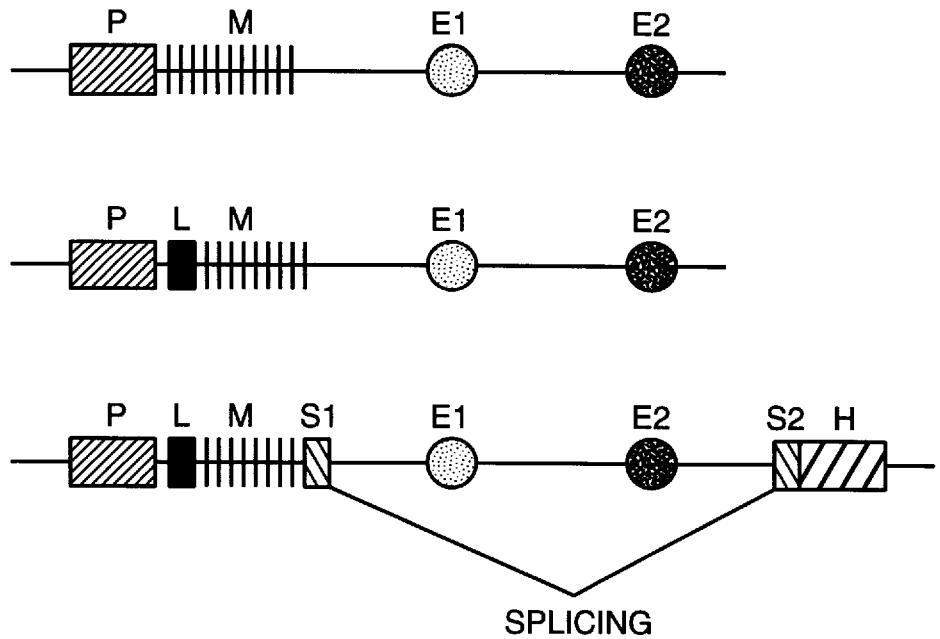
FIG. 1 is a schematic diagram of prototype cassettes for mutating proteins according to the invention. A typical plasmid includes a promoter, an immunoglobulin leader sequence (optional), a multiple cloning site (optional), the immunoglobulin heavy chain major intron enhancer and the 3' kappa immunoglobulin intron enhancer. The optional splice site and the his tag have been added to facilitate further manipulations of the selected clone.

The invention described here allows saturation mutagenesis to occur within a eukaryotic cell with minimal technical effort. Coupled with a selection system, it will yield a protein variant of interest without prior insight into what the structural modifications ought to be. This eukaryotic, high-rate mutagenesis system utilizes a hypermutation-competent expression vector containing immunoglobulin hypermutation elements transformed into a mutator cell line containing factors responsive to the hypermutation elements. The cellular factors respond to the hypermutation signals present on the vector, resulting in saturation mutagenesis of a target gene at a rate at or near $10^{-4}$/bp/generation.

The vector is constructed to permit the cloning of a target gene under the control of a promoter and in proximity to at least two immunoglobulin enhancer fragments. Other immunoglobulin genetic sequences can be present, but are not required. The target gene can generally be up to 4 Kb in length, preferably less than 3 Kb, and most preferably less than 2 Kb in length. In some cases the target gene can be greater than 4 kb in length, but this is less preferred. The promoter is any eukaryotic promoter, such as the thymidine kinase promoter; a promoter obtained from the genomes of viruses such as polyoma, SV40, adenovirus, retroviruses, hepatitis-B virus, cytomegalovirus; or any other promoter effective in mammalian cells. In some cases constitutive expression is preferred; in other cases an inducible promoter or one capable of binding a repressor is desirable. There are many promoters available in the art, including, e.g., the inducible promoter for the tetracycline resistance gene.

Definitions

"Hypermutation" is a mechanism by which mutagenesis occurs at a rate approaching that naturally occurring in the immunoglobulin variable region, which is preferably in the range of 10×4 to $10^{-3}$/bp/generation more preferably in the range of $5 \times 10^{-5}$ to $5 \times 10^{-4}$, and most preferably is $10^{-4}$/bp/generation but can sometimes be in the range of $5 \times 10^{-5}$ to $10^{-5}$/bp/generation.

A "hypermutation competent expression vector" is a vector containing a promoter, a cloning site for the insertion of a target gene, and elements required for hypermutation. Elements required for hypermutation include at least two immunoglobulin enhancers, which preferably can be independently the heavy chain large intronic enhancer fragment and the 3' kappa enhancer fragment. The enhancers can also be employed in a duplicative fashion; for example, a vector could contain two or more copies of the large intronic enhancer or two or more copies of the 3' kappa enhancer. The enhancers can preferably be used in the genomic 5' to 3' orientation and can also be used in the 3' to 5' reverse orientation, although this is less preferred in the case of the heavy chain enhancer fragment.

The "heavy chain large intronic enhancer fragment" is preferably the XbaI-EcoRI fragment described in Grosschedl et al. and can be one or more subfragments determined to have hypermutation activity.

The "3' kappa (K) enhancer fragment" is preferably the ScaI-XbaI fragment described in Meyer et aL and can be one or more subfragments determined to have hypermutation activity.

A "mutator positive cell line" is a cell line containing cellular factors that are sufficient to work in combination with enhancers to effect hypermutation. The cell line can be of pre-B lymphocyte origin, such as 18–81, or can be a cell line transfected with factors determined to effect hypermutation.

In a preferred embodiment, the invention uses heavy chain large intronic enhancer fragment and a kappa light chain 3' enhancer fragment. Alternatively, the vector contains two or more of either enhancer fragment alone or in combination with one or more of the other. For example, at least two heavy chain enhancer fragments or at least two κ enhancer fragments can be used. In another embodiment, although less preferred, two or more of either the heavy chain enhancer fragment or the κ enhancer fragment can be used in the absence of the other. In a preferred embodiment, both enhancers are positioned at a location 3' of the target gene. When both the heavy chain enhancer fragment and the κ enhancer fragments are positioned 3' relative to the target gene, it is preferred that the heavy chain enhancer fragment be located in greater proximity to the target gene than the κ enhancer fragment. The 5' end of the heavy chain large intronic enhancer fragment can be positioned up to 3 kb 3' of the 3' end of the target gene, preferably less than 2 kb, more preferably less than 1 kb, and most preferably immediately adjacent to the target gene. The heavy chain enhancer fragment can be positioned greater than 3 kb 3' of the target gene, but this is less preferred. The K enhancer fragment can be located in greater proximity to the target gene than the heavy chain enhancer fragment, but this is less preferred. The 3' κ enhancer fragment can be located up to 20 kb and preferably 5–15 kb 3' of the heavy chain large intronic enhancer. The 3' κ enhancer fragment can be located as close as 1 kb 3' of the heavy chain large intronic enhancer fragment, but this is less preferred. In another preferred embodiment, the 3' kappa enhancer fragment is located 5' relative to the target gene. The large intronic enhancer fragment can also be positioned 5' relative to the target gene, although this embodiment is less preferred.

In a preferred embodiment, the enhancer fragments are present in a genomic orientation. The enhancer sequence present in the genomic immunoglobulin gene is present in a "genomic orientation." If it is flipped in the construct so that it now appears in a 3' to 5' orientation (as opposed to the 5' to 3' orientation in the native genomic configuration), it is present in the "reverse orientation." However, the κ enhancer fragment can be present in reverse orientation. The heavy chain enhancer fragment can also be present in reverse orientation, but this is less preferred.

One preferred embodiment utilizes the ScaI-XbaI kappa 3' enhancer fragment, approximately 800 bp in size (Meyer et al., EMBO Journal Vol. 8, no. 7 p. 1959–1964 [1989]), and the XbaI-EcoRI heavy chain large intron enhancer, approximately 600 bp in size (Grosschedl et al., Cell Vol 41, 885–897 [1985]). Another embodiment utilizes hypermutation-competent fragments of one or both enhancers. Hypermutation-competent fragments can be identified in a number of ways. One way is to perform deletional analysis by constructing hypermutation cassettes containing various enhancer deletion mutants and a reporter gene. The hypermutation efficacy of the enhancer deletion mutant can be assessed by determining the rate of mutation of the reporter gene. Deletion mutants can be prepared in a variety of ways. Oligonucleotides can be designed containing fragment sequences to be tested. Alternatively, a more random approach is to linearize the expression vector by restriction digest within an enhancer, followed by subsequent exonuclease treatment and religation. Yet another method is to simply use restriction digests to remove sections of DNA.

The vector can also contain a selectable marker, such as neo$^r$, to identify transformed eukaryotic cells. The vector can also contain an origin of replication and a selectable marker effective in bacterial cells to facilitate the cloning process. If desired, a tag may be included in the vector construct to facilitate purification. Heterologous genetic material encoding any number of peptide fragments could be tagged onto the target gene sequence. Preferably, the peptide fragments are capable of binding some moiety that can be immobilized on a matrix. The protein product of the target gene can then be purified by binding the fusion protein to the matrix via the tag sequence. Some examples include the use of a histidine tag, a peptide moiety known to bind heparin, an epitope specific for a particular antibody, etc. So that the tag sequence is not subject to hypermutation, in preferred embodiments the tag sequence is positioned 3' of the hypermutation region, and splice/donor sites are provided so that the tag sequence can be fused with the coding sequence of the target gene prior to translation of the mRNA.

A "mutator positive cell line," also referred to herein as a "mutator cell line," is a cell line containing cellular factors that work in combination with enhancers to effectuate hypermutation. The cell line is preferably of pre-B lymphocyte origin, and most preferably of murine origin, or it can be a cell line transfected with factors determined to effectuate hypermutation. One way to produce a cell line transfected with a factor required for hypermutation is to construct a cDNA library in a hypermutation-competent vector containing a reporter gene. The cDNA can be prepared by conventional techniques from a mutator-positive cell line. The cDNA-reporter library construct is then transfected into a mutator-negative cell line, hypermutation is allowed to proceed as the transfectant cells are grown to a desired density, and the resultant pool is screened for a mutant phenotype. Alternatively, a vector pool containing the cDNA library can be co-transfected with the hypermutation reporter vector. Another way to make a mutator-positive cell line is to narrow the cDNAs tested to those encoding proteins known to bind E-boxes within various enhancers. It is possible that more than one factor might be required for hypermutation activity, and consequently, initial mutation rates can be expected to be less than $10^{-4}$/bp/generation, but should be greater than $10^{-7}$/bp/generation. It is also possible that some factors may be composed of polypeptide subunits and expression cloning procedures could be modified to achieve complementation.

Saturation mutagenesis of a target gene would typically proceed as follows. The target gene is cloned into a hypermutation cassette of an expression vector, and the resulting construct is then used to transform a mutator cell line such as 18–81. Transformed cells are cultured to a maximal density while mutagenesis occurs. These cells can be concentrated by centrifugation if desired, or they may be used directly in a mutant selection system. The particular selection system employed will vary according to the properties of the protein product of the target gene and is not the point of novelty of the invention. Typically, one factor of an interaction of interest will be immobilized, and the other factor will be expressed either on the surface of the mutator cell or in soluble form. In one embodiment, the target protein is expressed on the surface of the transformed cell. Under these circumstances, those mutant cells that bind with specificity can be recovered and cultured. Mutants of interest can be identified by utilizing any of a number of selection systems widely used in the art. Some examples include labelling cells with a detectable marker such as a fluorescent dye and allowing binding to occur between the mutant protein on the cell surface and its binding partner. If the binding partner has been immobilized on a plate, a suitable detection system, e.g., a fluorimeter, can be used to identify wells containing a mutant of interest. Alternatively, the binding partner can be labelled with a fluorescent tag, and cells expressing a mutant of interest can be sorted using a fluorescence activated cell sorter. To prevent repeated mutation after selection in preferred embodiments hypermutation is arrested prior to culturing the selected cells. This can be accomplished in a number of ways, including fusion to a myeloma or repression of an inducible promoter.

Most groups have found that fusion to a myeloma eliminates the hypermutation capability that is possessed by a cell line derived from pre-B lymphocytes. It has been previously reported that immunoglobulin genes are not hypermutable in hybridomas (Milstein et al., National Cancer Institute Monographs 48, 321–330 [1978]; Adetugbo et al., Nature 265, 299–304 [1977]; Shulman et al., Molec. Cell. Biol. 2, 1033–1043 [1982]; Wabl et al., Proc. Natl. Acad. Sci. USA 82, 479–482 [1985]). The present inventors also reported that when 18–81 was fused to the mouse plasmacytoma Ag 8.653, the resulting hybridoma showed no hypermutation (Wabl et al., Proc. Natl. Acad. Sci. USA 82, 479–482 [1985]). The fusion does not interfere with the expression of the gene of interest, but it arrests the random mutagenesis. There is, however, one anomalous group that reports a high rate of mutation in a hybridoma (Green et aL, Proc. Natl. Acad. Sci. USA 92:6304–6308 [1995]).

Example 5 (below) demonstrates the use of repression of an inducible promoter to arrest hypermutation. Alternatively, the mutant of interest can be amplified in whole or in part by polymerase chain reaction, using oligonucleotides that will anneal to locations outside the region of hypermutation or within the gene itself. Then the mutagenized DNA fragment can be subcloned for other purposes, such as expression, purification, or characterization. In another embodiment, the target protein can be expressed in soluble form. The conditioned media from the transfected cells can be concentrated if desired and applied to the selection system. Specific binders can be identified directly or indirectly, for example by antibody recognition of either the target gene itself or an attached tag sequence. The mutants of interest can then be further characterized by a number of protein chemistry techniques such as microsequencing.

The mutagenesis system can be used to effect in vitro the affinity maturation of antibodies. In one aspect, the invention may be applied toward improving the affinity of antibodies from "naive," i.e., non-immune, phage human antibody libraries. Such libraries already exist and yield antibodies to any antigen. However, since they are made from nonimmunized individuals, their affinities are low. In another aspect of the invention, the affinity of antibodies that were generated by conventional hybridoma techniques can be improved by applying a high rate mutagenesis system of the invention to the isolated gene encoding for the initial low-affinity antibody. These enhanced-affinity antibodies can be utilized as improvements over many antibody-based diagnostics and therapeutics currently available.

The mutagenesis system can also be used to effect receptor or ligand modification. In one aspect, the invention can generate a ligand or receptor with enhanced binding characteristics for its corresponding receptor or ligand. In another aspect, the mutagenesis system can be used to generate an inhibitor of functional receptor-ligand interaction by creating a ligand or receptor that still binds, but does not elicit a functional response. In yet another aspect of the invention, multiple biologically active variants of a target protein can be identified and recovered, thereby providing a means to study structure-function relationships of the protein. Additionally, species diversity can be investigated by comparing results obtained by selections utilizing receptors or other molecules from different species.

A receptor or ligand can be modified such that it can still bind, but does not signal any more. For example, the gene encoding the Fas ligand can be cloned into the mutator cassette and transfected into mutator cell line 18–81. Cells are grown to numbers high enough to accumulate mutations, during which time apoptosis is prevented by inhibitors. Cells are cloned by limiting dilution, and the inhibitor is taken off. Then all the clones with non-mutated Fas ligand will undergo apoptosis, but the clones with non-functional Fas ligand will be spared. As long as they still bind to the Fas receptor, these non-functional Fas ligands could be, for example, introduced into the cells of an organ to be transplanted and thus prevent graft rejection.

Alternatively, a better signalling ligand can be selected, which would provide a lower effective dosage of a pharmacologically active therapeutic. For example, the gene encoding erythropoietin can be cloned into the mutator cassette and transfected into mutator cell line 18–81. The cells are grown for some time to accumulate somatic mutants. When the culture has reached $10^7$ cells per ml it can be expected that each site in the erythropoietin gene is mutated, the mutations being present in different cells. Then the 18–81 cells are plated onto dispersed bone marrow cells grown in culture. The erythropoietin produced by the 18–81 cells will allow the formation of colonies founded by erythrocyte colony-forming units; a different class of larger colonies will be observed at a site where either substantially more or a better-binding erythropoietin is produced.

EXAMPLES

Example 1 Plasmid Constructs

Plasmids phyp #1 and #2 were generated by exchanging the original variable region of the plasmid pμ (Grosschedl et al., Cell 38, 647–658 [1984]) with the rearranged V2 variable region of the cell line 18–81. The neomycin resistance gene was cloned as a SalI/XhoI cassette 5' to the V region. A Sac I-Xba I fragment containing the 3' κ enhancer (Meyer et al., Nucleic Acids Research 18, 5609–5615 [1990]; Meyer et aL, EMBO Journal 8, 1959–1964 [1989]) was cloned into the XhoI site 3' of the μ membrane exons. For stable transfection the construct was linearized at the SalI site adjacent to the neomycin resistance gene. To generate plasmid ptk-LacZ-Stop the tk promoter from plasmid pMClneo (Thomas et al., Cell 51, 503–512 [1987]) was cloned as a XhoI/PstI fragment together with a SalI/XhoI fragment of the lacZ gene into the BS/KS vector (Stratagene). A termination codon had been introduced before into the lac Z gene by oligonucleotide site-directed mutagenesis at a position 161 nucleotides 3' to the Kpn I site. The $neo^r$ gene was cloned as a XhoI-SalI fragment into the SpeI site of BS/KS-tk-LacZ-Stop. For stable transfection the ptk-LacZ-Stop plasmid was linearized with XhoI.

Example 2 Detection and Quantitation of Mutants

Plasmids phyp #1 and #2 were transfected into clone 18–81.AM (Jack et al., Proc. Natl. Acad. Sci USA 85, 1581–1585 [1988]), and transfectants were subcloned under limiting dilution conditions. The clones were grown to $10^6$ cells and μ producing revertants were counted per $10^5$ cells using immunofluorescence. For the clones transfected with lacZ containing the termination codon the cells were expanded in a 24 well plate to 1–2×$10^6$ cells/well, and all cells in a well were analyzed for β-galactosidase activity.

For immunofluorescence, $10^5$ cells were spun onto a slide, ethanol fixed and rehydrated in PBS+1% BSA; cells were stained with FITC-conjugated goat anti-mouse IgM antibody (Fisher) and washed 3 times 10 min in PBS.

β-galactosidase activity was monitored with either the chromogenic substrate 5-bromo-4-chloro-3-indolyl -β-D- galactoside (X-Gal) or the fluorogenic substrate fluorescein di-β-D-galactopyranoside (FDG). For staining with X-Gal, the cells were fixed for 5 min at room temperature in the culture wells or on slides with phosphate buffered saline (PBS) containing 2% formaldehyde and 0.2% glutaraldehyde. After washing in PBS, the cells were stained with PBS containing 5 mM potassium ferricyanide, 5 mM potassium ferrocyanide, 2 mM $MgCl_2$, and X-Gal at a final concentration of 1 mg/ml. With this procedure, the cytoplasm of positive cells is stained bright blue within 1 to 24 hr at 37° C. To verify the nature of a beta galactosidase expressing cell, one transfection clone was selected for enrichment and purification of its revertant cells by FACS sorting (Nolan et al., Proc. Natl. Acad. Sci. USA 85, 2603–2607 [1988]) and subsequent subcloning. The revertant tested was missing the Bcl I restriction site that we had introduced and of which the opal codon TGA was part.

Example 3 Cloning and Sequencing of Mutants

From six independent transfection clones (of 18–81. ΔM, an 18–81 subclone with no endogenous $C\mu$) some revertants and some of their $\mu$ negative sister cells were cloned and the sequence of their D region was determined. Clones containing constructs phyp #1 or phyp #2 with 25 to 500 revertants per $10^5$ cells were first sib-selected for enrichment of revertants and subsequently subcloned by seeding 30 cells per 96 well plate. Pure revertant clones were expanded and total RNA was isolated. cDNA was synthesized using an oligo dT primer (dT17). Then DNA was amplified using a specific primer pair that covered sequences specific to V81X (GAAGAGGCTGGAGTTGGTCGCAG) and $c\mu4$ (CACACTGATGTCTGCAGGAGAGAAGC), respectively. The PCR product was agarose gel-purified and directly sequenced using the V81X primer. PCR procedures and sequencing were done on coded samples, i.e., without knowledge of to which clone they belong—to one of the 7 revertants or to one of the 6 sister cells containing the TAG codon. In all cases the codon in position 101 corresponded to the status of $\mu$ chain expression, i.e., the clones with TAC or TAT turned out to be $\mu$ chain expressors, whereas the clones with TAG did not express $\mu$.

Example 4 Cell Fusion with Myeloma

Because the 18–81 cells were not sensitive to HAT, a modification of the method of Wright and Hayflick was used to select against 18–81 cells that had not fused with the myeloma. Immediately prior to fusion, the 18–81 cells were washed twice in RPMI 1640 medium. Freshly prepared iodoacetamide (Sigma), 0.2M in distilled water, was added to give a final concentration of 2 mM. This concentration is 10-fold higher than the minimal does required to prevent growth of 18–81 cells. The cells were incubated for 25 min. at 37° C.; then fetal calf serum was added to a final concentration of 25% (vol/vol). The cells were centrifuged and washed twice in medium with 15% fetal calf serum and then once in serum-free medium prior to fusion. For fusion, the ratio of 18–81 cells to myeloma cells was 2:1. HAT was added 24 hrs. after fusion.

Unfused myeloma cells are eliminated by drug selection. Even in the most efficient hybridoma fusions, only about 1% of the starting cells are fused, and only about 1 in $10^5$ form viable hybrids. This leaves a large number of unfused cells still in the culture. The cells from the immunized animal do not continue to grow in tissue culture, and so, do not confuse further work. However, the myeloma cells are well adapted to tissue culture and must be killed. Most hybridoma constructions achieve this by drug selection. Commonly, the myeloma partner has a mutation in one of the enzymes of the salvage pathway of purine nucleotide biosynthesis (first reported by Littlefield 1964). For example, selection with 8-azaguanine often yields a cell line harboring a mutated hypoxanthine-guanine phosphoribosyl transferase gene (HPRT). The addition of any compound that blocks the de novo nucleotide synthesis pathway will force cells to use the salvage pathway. Cells containing a nonfunctional HPRT protein will die in these conditions. Hybrids between myelomas with a nonfunctional HPRT and cells with a functional HPRT will be able to grow. Selections are commonly done with aminopterin, methotrexate, or azaserine.

Mutations in the HPRT gene can be selected by growing cells in the presence of purine analogs such as 8-azaguanine (8-AG). HPRT will recognize 8-AG as a substrate and convert it to the monophosphate nucleotide. The 8-AG-containing nucleotide is then processed further and incorporated into DNA and RNA, where it is toxic. Therefore, cells with a functional HPRT enzyme grown in the presence of 8-AG will die. However, because the HPRT enzyme is a part of a nonessential pathway (the de novo pathway is capable of supporting good cell growth in tissue culture), cells harboring a mutant HPRT gene can continue to grow. Therefore, selection with 8-AG will kill cells with a wild-type HPRT, but will not affect cells with a mutant HPRT.

The HPRT gene is found on the X chromosome, so the normal rate of mutagenesis in mammalian cells is sufficiently high to produce one cell bearing a nonfunctional HPRT in approximately $10^7$ cells. Therefore, no mutagenesis is necessary to select for the HPRT-negative phenotype, making selection relatively simple. $10^8$ or more cells are treated with 8-AG, and surviving cells are tested for the loss of HPRT.

1. Grow approximately 108 cells in standard tissue culture medium.
2. If the cells do not adhere to plastic, centrifuge the cells at 400 g for 10 min. Resuspend the cell pellet in 100 ml of medium supplemented with 20 $\mu$g/ml of 8-AG and transfer to 10×100-mm dishes. If the cells adhere to plastic, grow the cells to 80% confluence and remove the medium by aspiration. Feed the cells with fresh medium supplemented with 20 $\mu$g/ml of 8-AG.

Example 5 Repression of Inducible Promoter

The tetracycline operon inducible promoter requires a transactivator to induce or trigger expression. The transactivator is a fusion protein containing a tetracycline promoter/operator binding site or domain and the VP16 transactivator domain. You can inhibit the binding of the transactivator to the tetracycline operon promoter by adding tetracycline to the tissue culture cells. The tetracycline blocks the binding site of the transactivator and the tetracycline operon promoter is turned off.

Example 6 Vector Construction and Transfection

The LacZ gene, a 3 Kb gene encoding for β-galactosidase, is cloned XhoI-SalI under the control of the tk promoter in a vector whose backbone is derived from Bluescript BS/KS (Stratagene). The large intronic enhancer is positioned immediately adjacent to the 3' end of LacZ, utilizing the restriction sites XbaI/EcoRI. A DNA spacer fragment, whose sequence is unimportant, positions the ScaI-XbaI 3' κ enhancer fragment 2 Kb 3' of the heavy chain large intronic enhancer fragment. 18–81 cells are then electroporated and transfectants selected for neomycin resistance.

Example 9 FDG Staining for β-Galactosidase

Exponentially growing fibroblast cells were treated with trypsin (GIBCO no. 610–5400; diluted to 1×solution) in phosphate-buffered saline until they could be removed from the plate with mild agitation. BW5147 and SP2/0 suspension cells in exponential phase were pelleted and resuspended in phosphate-buffered saline. Cells for staining were counted and brought to $10^7$ per ml in RPMI 1640-deficient medium (no. 9826, Applied Scientific, San Francisco) containing 2% (vol/vol) fetal calf serum. 10 mM Hepes (pH 7.3). The protocol for staining cells is as follows: (i) add 100 µl of cells at $10^7$ per ml to a 5-ml polystyrene tube; (ii) bring the cell suspension to 37° C. in a water bath for 5 min; (iii) add 100 µl of 2 mM FDG in $H_2O$, prewarmed to 37° C.; (iv) mix gently but thoroughly and rapidly place back into the 37° C. water bath for 1 min; and (v) place the tube on ice and add 1800 µl of ice-chilled isotonic incubation medium and 1 µM propidium iodide.

Example 10 X-gal Staining

Spin approximately $10^5$ cells onto a slide or cells can be allowed to form a monolayer on the slide. Rinse in PBS. Transfer slides to a coplin jar and fix with 2% formaldehyde, 0.2% glutaraldehyde in PBS for 5 minutes at room temperature. Wash once in PBS for at least 10 minutes. Dry the slides around the cells. Add one to two drops of a staining solution composed of 5 mM potassium ferrocyanide, 5 mM potassium ferricyanide, 2 mM $MgCl_2$, 1 mg/ml X-gal in PBS. Apply coverslip. Incubate one to twenty-four hours at 37° C. in a wet chamber. Positive cells are bright blue in the cytoplasmic region.

Example 11 FACS Analysis based on β-Galactosidase Activity

Cells are stained with the β-galactoside analog fluorescein di-β-D-galactopyranoside (FDG) in a protocol termed "FACS-FDG" (Nolan et al, Proc. Natl. Acad. Sci. Vol 85:2603–2607 [1988]). The FDG is cleaved by β-galactosidase in $LacZ^+$ cells to yield fluorescein, which can be detected by the fluorescence activated cell sorter (FACS) and various clones can be sorted according to their level of expression.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A hypermutation competent expression vector comprising:

a promoter; and at least two immunoglobulin enhancer fragments, wherein at most one of said enhancer fragments is a kappa enhancer fragment.

2. A hypermutation competent expression vector comprising:

a promoter;

a heavy chain large intronic enhancer fragment; and a 3' kappa enhancer fragment.

3. A hypermutation competent expression vector comprising:

a promoter;

a heavy chain intronic enhancer fragment; and a 3' kappa enhancer fragment, wherein both enhancer fragments are located 3' of said promoter and are present in a genomic orientation.

4. A hypermutation competent expression vector comprising:

a promoter;

a heavy chain intronic enhancer fragment located 3' of said promoter and present in a genomic orientation; and a 3' kappa enhancer fragment.

5. A hypermutation competent expression vector comprising:

a promoter;

a heavy chain intronic enhancer fragment; and a 3' kappa enhancer fragment, wherein both said enhancer fragments are located 3' of said promoter.

6. A hypermutation competent expression vector comprising:

a promoter;

a heavy chain intronic enhancer fragment; and a 3' kappa enhancer fragment, wherein both said enhancer fragments are present in a genomic orientation.

7. A hypermutation competent expression vector comprising:

a promoter; and at least two hypermutation-effective immunoglobulin enhancer fragments, wherein at most one of said enhancer fragments is a kappa enhancer fragment.

8. The vector of claim 1, 2, 3, 4, 5 or 6 having a target gene inserted so as to be controlled by said promoter.

9. A mammalian host cell transformed with the vector of claim 8, wherein said host cell is obtained from a mutator positive cell line.

10. The mammalian host cell of claim 9, wherein said mutator positive cell line is selected from the group consisting of B cells and cells of the B lineage.

11. The host cell of claim 10, wherein said mutator positive cell line is of pre-B lymphocyte origin.

12. The host cell of claim 11, wherein said mutator positive cell line is 18–81.

13. The vector of claim 2, wherein said heavy chain intronic enhancer fragment is a fragment about 600 bp in size.

14. The vector of claim 13, wherein said fragment is an XbaI-EcoRI fragment.

15. The vector of claim 2, wherein said 3' kappa enhancer fragment is a fragment about 800 bp in size.

16. The vector of claim 15, wherein said fragment is a ScaI-XbaI fragment.

17. The vector of claim 15, wherein said heavy chain intronic enhancer fragment is a fragment about 600 bp in size.

18. The vector of claim 17, wherein both said enhancer fragments are present in a genomic orientation.

19. The vector of claim 18, wherein both said enhancer fragments are located 3' of said promoter.

20. The vector of claim 19, wherein said heavy chain enhancer fragment is located in greater proximity to said target gene than said kappa enhancer fragment.

21. The vector of claim 20, wherein the 5' end of said heavy chain enhancer fragment is positioned at most 3 Kb 3' of the 3' end of said target gene.

22. The vector of claim 21, wherein said kappa enhancer fragment is located 5 to 15 Kb 3' of said heavy chain enhancer fragment.

23. The vector of claim 17, wherein said promoter is a eukaryotic promoter.

24. The vector of claim 23, wherein said promoter is an inducible promoter.

25. The vector of claim 23, wherein said promoter is a thymidine kinase promoter.

26. The vector of claim 23 further comprising a target gene inserted so as to be controlled by said promoter.

27. The vector of claim 26, wherein said target gene is at most 4 Kb in length.

28. The vector of claim 27, wherein said heavy chain enhancer fragment is present in a genomic orientation, the 5' end of said heavy chain enhancer fragment is positioned at most 3 Kb 3' of the 3' end of said target gene, and said kappa enhancer fragment is located 5 to 15 Kb 3' of said heavy chain enhancer fragment.

29. The vector of claim 28, wherein said promoter is a thymidine kinase promoter.

30. A mammalian host cell transformed with the vector of claims 27, 20 or 28, wherein said host cell is obtained from a mutator positive cell line.

31. The mammalian host cell of claim 30, wherein said mutator positive cell line is of pre-B lymphocyte origin.

32. The mammalian host cell of claim 31, wherein said mutator positive cell line is 18–81.

33. The vector of claim 2 further comprising a selectable marker.

* * * * *